United States Patent [19]

Stark et al.

[11] Patent Number: 5,568,400
[45] Date of Patent: Oct. 22, 1996

[54] MULTIPLICATIVE SIGNAL CORRECTION METHOD AND APPARATUS

[76] Inventors: Edward W. Stark, Suite 3M - 160 W. End Ave., New York, N.Y. 10023; Harald Martens, Gamle Vegen 13, N-1430, Aas, Norway

[21] Appl. No.: 572,534

[22] Filed: Aug. 28, 1990

Related U.S. Application Data

[63] Continuation-in-part of Ser. No. 402,038, Sep. 1, 1989, abandoned.
[51] Int. Cl.[6] .......................... G06F 17/00; G06F 159/00
[52] U.S. Cl. ........................ 364/498; 364/571.02
[58] Field of Search ........................ 364/498, 570, 364/571.01, 571.02, 571.04, 572, 573, 574; 73/1 R; 356/326

[56] References Cited

U.S. PATENT DOCUMENTS

| | | | |
|---|---|---|---|
| 4,627,014 | 12/1986 | Lo et al. | 364/571.01 |
| 4,642,778 | 2/1987 | Hieftje et al. | 364/498 |
| 4,744,657 | 5/1988 | Aralis et al. | 364/571.04 X |
| 4,782,456 | 11/1988 | Poussier et al. | 364/574 |
| 4,802,102 | 1/1989 | Lacey | 364/497 |
| 4,884,213 | 11/1989 | Iwata et al. | 364/571.01 X |
| 4,916,645 | 4/1990 | Wuest et al. | 364/571.01 X |
| 4,975,581 | 12/1990 | Robinson et al. | 250/339 |
| 5,046,846 | 9/1991 | Ray et al. | 364/498 X |
| 5,081,597 | 1/1992 | Kowalski | 364/571.02 X |
| 5,083,283 | 1/1992 | Imai et al. | 364/571.02 X |
| 5,369,578 | 11/1994 | Roscoe et al. | 364/422 |

OTHER PUBLICATIONS

Martens et al. "Multivariate Linearity Transformations for Near Infra-Red Reflectance Spectrometry" pp. 289–318, Jun. 1983.

Food Research and Data Analysis edited by Harald Martens Hellmut Russwurm, Jr.; Applied Science Publishers, Ltd 1983.

Optimization of Mathematical Treatments of Raw Near-Infrared Signal in the Measurement of Protein in Hard Red Spring Wheat. I. Influence of Particle Size Cereal Chemistry, vol. 61, No. 2, 1984.

Animal Reed Evaluation by Near Infrared Reflectance (NIR) Spectrometer Mar. 23, 1982; Murray et al.

A New Method for Obtaining Individual Component Spectra from Those of Complex Mixtures –D. E. Honigs, G. M. Hieftje, and T. Hirschfeld Applied Spectroscopy, Aug. 1983.

Multivariate Linearity Transformations for Near-Infrared Reflectance Spectrometry –Harald Martens, Svend Age Jensen and Paul Geladi Jun. 1983.

A Pathlength Correction Method for Near-Infrared Spectroscopy by Charles E. Miller and Tormod Naes Applied Spectroscopy vol. 44, No. 5, 1990.

*Primary Examiner*—Michael Zanelli
*Attorney, Agent, or Firm*—McAulay Fisher Nissen Goldberg & Kiel, LLP

[57] ABSTRACT

An improved method and apparatus are disclosed for processing spectral data to remove undesired variations in such data and to remove interfering information present in the data. The method land apparatus corrects multiplicative effects present in the spectral data. Additive and interferent contributions can be corrected as well. In one aspect of the method, coefficients for a selected appropriate model are applied to the input spectral data based on first and second reference spectra. The spectral data are then corrected based on the estimated coefficients at least as to multiplicative errors for producing a linear additive structure for use in calibration, validation and determination by linear multivariate analysis. The method and apparatus will improve the accuracy of spectral data structures derived from measurements Using spectroscopy, chromatography, thermal analysis, mechanical vibration and acoustic analysis, rheology, electrophoresis, image analysis and other analytical technologies producing data of similar multivariate nature.

49 Claims, 5 Drawing Sheets

FIG. 4 COEFFICIENT ESTIMATOR 320

PRINCIPAL COMPONENTS REGRESSION (PCR)

MULTIPLICATIVE SIGNAL CORRECTION METHOD AND APPARATUS

CROSS REFERENCE TO RELATED APPLICATIONS

This is a continuation-in-part application of application Ser. No. 07/402,038, filed Sep. 1, 1989, now abandoned.

FIELD OF THE INVENTION

The present invention relates generally to processing of spectral data to reduce undesired variations and to remove interfering information present in the data. Specifically, the present invention relates to an improved instrument or method for processing of spectral data to reduce undesired variations and to remove interfering information present in the data. Most specifically, the present invention relates to an improved instrument, method or process to provide improved measurements of analytes based on spectral data by reducing Undesired variations and removing interfering information present in the data.

BACKGROUND OF THE INVENTION

Spectral data consists of multiple interrelated data points, such as an optical spectrum or a chromatogram, which carries information related to the components and characteristics of the specimen from which the data was derived, as well as to performance of the analytical instrument and to the general experimental conditions. In spectroscopy, for example, this specimen is a material and the spectral data comprises the results of related measurements made on the specimen as a function of a variable, such as the frequency or wavelength of the energy used for measurement. In chromatography, the spectral variable may be time or distance. In thermal analysis, the variable is usually temperature or time. In mechanical vibration/acoustics analysis the variable is usually frequency. In rheology the variable can be position, shear rate or time. In electrophoresis and thin layer chromatography the variable is relative distance in one or two dimensions. In many different analyses, e.g. kinetic measurements, time is either the primary variable or an additional variable that adds to the dimensionality of the data.

In image analysis the fundamental variable is usually distance in one or two dimensions although the two-dimensional Fourier transform, also known as the Weiner transform, and the Weiner spectrum which express the information in a two-dimensional spatial frequency domain are also prevalent. Multivariate images, such as three color video signals and many satellite images where each picture element is characterized by a multichannel "spectrum" and also images constituting a time sequence of information, provide additional dimensionality in the data. Alternatively, in image analysis, the images can be summarized into histograms showing distributions of various picture elements, where the variable is then a vector of categories, each representing a class of picture elements, e.g. various gray levels of pixels, or contextual classes based on local image geometry. For multivariate images, the additional multichannel information may be included in the contextual classification. Time information can likewise be included in the definition of the categories in the variable. The above descriptions of two-way images also apply to three-way tomographic images, e.g. in MRI and X-ray tomography.

It should also be noted that it is possible to express spectral data more or less equivalently in several different domains, i.e. with respect to several different variables, for example by a Fourier, Weiner, or Hadamard transformation, and using different metrics, such as Euclidian and Mahalanobis distances.

For all of the above types of spectral data, information from several specimens may be related to each other statistically to derive analytical information. In order to derive specific desired analytical information, such as the concentration of a constituent, the magnitude of a physical property, or the identification of the specimen or its components, one form or another of additive multivariate approximation or modeling is typically employed. For example, a desired parameter may be modeled as the suitably weighted sum of the measurements at selected data points within the spectrum or a weighted sum of previously determined reference spectra. The weighting coefficients, sometimes referred to as the calibration coefficients, are statistically determined based on spectral data obtained from a set of calibration specimens for which the values for the parameter of interest are known.

This additive multivariate calibration may be considered as a general interference subtraction, whereby each input spectrum is resolved as a sum of underlying structures, each with a known or estimated spectrum. The structures can be known or directly measured spectra of various individual phenomena affecting the input spectrum, or estimated "loading" vectors (e.g. bilinear factors) that span their variability statistically. The resolution yields estimates of the level or score of each such phenomenon or factor in the input spectrum. Then the additive modeling performs the equivalent of a weighted subtraction of the various interferants' spectral effects, thereby providing selectivity enhancement.

Additive multivariate approximation is appropriate for purely additive structures, or by taking the logarithm of the data values, for purely multiplicative structures. The modeling is much less accurate and robust for mixed additive and multiplicative structures. Unfortunately, real measured spectral data usually has some degree of such mixed structures including multiplicative effects that affect the analytical sensitivity. In diffuse reflectance spectroscopy, for example, the scatter coefficient varies due to particle size. Even when grinding is appropriate, the resulting particles have a range of sizes, with a mean and distribution that is variable depending on both physical and chemical factors, and a range of optical properties that vary with the wavelength itself as well as the particle composition and physical shape. In transmission spectroscopy, the effective optical pathlength may be affected by changes in geometry, scattering, temperature, density of the material, and related physical parameters. Variation in the amount of material added to the column produces multiplicative effects in chromatography as does the intensity of the dye added to gel in electrophoresis. In image analysis, variations the total area of pixels counted and the pixel intensity can contribute multiplicative factors to otherwise additive structures. Finally, instrumental and other experimental effects, e.g. a nonlinear instrument response, may appear as multiplicative factors, particularly when a logarithmic data transformation is applied.

Much of the effort to overcome these effects has resulted from the increased use of near-infrared diffuse reflectance spectroscopy, in Which multiplicative effects are quite large although not necessarily obvious on first examination of spectral data. Near-infrared spectra tend to decrease in absorbance with decreasing wavelength because the absorption bands are based on several orders of overtones and combinations of mid-infrared vibrational frequencies. Band strength decreases as the order of the harmonic involved increases, i.e. as the frequency increases. A multiplicative effect on such a tilted spectrum appears similar to the addition of a tilted baseline. Therefore, Norris and other early workers used the first or second derivative of the absorbance spectrum with respect to wavelength in their models. The derivatives explicitly remove any additive constant and, in the case of the second derivative, any linear sloped additive baseline. Unfortunately, the true multiplicative effects remain after taking the derivative of the data.

Removal of a multiplicative factor implies division of the data by an appropriate value. Norris (K. H. Norris and P. C. Williams, Optimization of Mathematical Treatments of Raw Near-Infrared Signal in the Measurement of Protein in Hard Red Spring Wheat. I. Influence of Particle Size, Cereal Chem. 61(2):158 and K. H. Norris, Extracting Information from Spectrophotometric Curves Predicting Chemical Composition from Visible and Near-Infrared Spectra, Food Research and Data Analysis, H. Martens and H. Russwurm, Ed. Applied Science Publishers, Ltd. 1983 Essex, England, copies of which being annexed hereto) introduced the use of derivative ratios by 1981. In their approach, first or second derivative spectra are used so that any baseline offsets are eliminated. The absence of baseline offset in the divisor is a requirement to maintain linearity when removing a multiplicative factor. Their method involves selecting a wavelength for the first numerator by examination of the correlation of the data at each wavelength with the values of the parameter of interest. A denominator wavelength is then selected by similar examination of the correlation of the ratio to the parameter of interest. Iteration involving changes to the data point spacing and smoothing used in the finite difference computation of the derivative is then performed to optimize the approximation. Additional terms may then be added to the model in a stepwise procedure. This method has been useful however, it is limited to a specific calibration using data at a few selected wavelengths.

Murray and Jessiman (I. Murray and C. S. Jessiman, unpublished work (1982) quoted in Animal Feed Evaluation by Near Infrared Reflectance (NIR) Spectrocomputer paper presented at the Royal Society of Chemistry Symposium at the University of East Anglia, Norwich UK 23 Mar. 1982. A copy of which being annexed hereto) developed a technique termed "mathematical ball milling" which provided a correction to the whole spectrum. In their technique, simple linear least squares regression (estimation of a multiplicative slope and additive offset parameter) is used to find the best linear fit of each spectrum, as well as of the average of many spectra, (ordinates or regressands) to a vector representing the actual wavelength, e.g., nanometers (common abscissa or regressor). Each individual spectrum is then modified with respect to offset and slope such that the simple linear regression line of the modified spectrum is coincident with the regression line initially obtained for the average spectrum.

Martens, Jensen and Geladi (H. Martens, S. A. Jensen, and P. Geladi, Multivariate Linearity Transformations for Near-Infrared Reflectance Spectrometry, Proceedings, Nordic Symposium on Applied Statistics, Stavanger, June 1983, Stokkand Forlag Publishers, Stavanger, Norway pp.205–234, a copy of which being annexed hereto) developed the method of "Multiplicative Scatter Correction" that is the forerunner of the present invention. They utilize a previously known reference spectrum representative of the "ideal specimen". In practice this is usually based on the average of the spectra contained in the calibration data set. Each spectrum, whether used for calibration, validation, or determination, is then projected on this average spectrum by simple linear regression over selected wavelengths and its offset and slope relative to the average spectrum thereby determined. Corrected spectra are then obtained by subtracting the appropriate offset coefficient from each spectrum and then dividing the resulting spectral data by the slope coefficient. The estimated slope coefficient is sometimes modified somewhat at different wavelengths in order to correct for wavelength dependency of the scatter coefficient. The resulting corrected spectral values equal the average spectral values plus residuals that contain the desired analytical information normalized to the average measurement conditions. This method, however, is subject to errors caused by the non-random nature and potentially large magnitude of these residuals.

A prior approach to minimizing these errors has been to omit those portions of the spectrum having large variability from the data used in the regression. This approach is sometimes difficult to apply, because it may require many trials and operator judgments, and it is only partially successful at best. In a variation of this approach, the range of the spectral data included in the average spectrum used to determine the offset and slope coefficients is restricted to the vicinity of a strong isolated spectral feature, such as a solvent absorption band, thereby limiting the magnitude of the residuals and improving the accuracy of the correction. This variation has been applied to correction of the effects of scattering within the specimen in transmission spectroscopy. In many cases, however, there is no strong isolated band available for determination of the multiplicative correction. A related problem occurs in measuring one material through another with the pathlength through each material unknown and variable. In either case, better means are needed to accurately separate additive and multiplicative effects.

Varying levels of known or unknown additive interferences also characterize the above forms of spectral data. In spectroscopy it is common to have a background spectrum added to the desired data from sources such as absorption by the solvent used to dissolve the specimen for analysis, absorption by the reference used to determine the incident energy, nonspecific emission or fluorescence from the specimen or instrumentation, and stray light, specular reflections, and other measurement artifacts. The other technologies discussed above have similar problems of additive interferences.

Specimen stability is often a cause of such a problem. For example, in near-infrared diffuse reflectance spectroscopy powdered specimens are common. The water content of many powdered specimens tends to equilibrate with the environmental humidity. In many cases, it is extremely difficult to maintain an adequate set of calibration and validation specimens with a sufficient range of water content to allow accurate calibration. Temperature also affects the spectra, particularly in the case of hydrogen bonded species such as water. A small fraction of one degree Celsius temperature change can be readily detected in aqueous specimens. Adequate control of specimen temperature during measurement is difficult in the laboratory and often impossible in a processing plant environment. Other measurement technologies are subject to such difficult to control variables. A method to accurately remove the spectral effects of such variables without disturbing the analyte information prior to use of the spectra for calibration, validation, and determination would improve the utility and performance of multivariate data analysis techniques.

Manual subtraction of one or more background spectra from an unknown spectrum by graphically oriented trialand-error is well known in several disciplines, e.g. in UV, VIS, and IR spectroscopy. This type of interference subtraction has the advantage of letting the user interactively apply his or her knowledge of the structures involved. Automated methods have been developed but these are subject to significant errors, particularly where not all the constituent spectra are known, where constituent spectra are influenced by changes in the environment, and Where the background or interference spectra are correlated with the analyte spectra.

In general, the above previous spectral correction techniques have been based on assumptions that the data structures are linear in the parameters. Various linearization techniques are applied to the data, most commonly the logarithmic transformation to convert purely multiplicative structures to additive form and, in diffuse reflectance spectroscopy, the Kubelka-Munk function. While useful, these data transformations are based on the assumption that the structure is intrinsically linear. Physical and instrumental effects often add intrinsically nonlinear elements to measured data structures, even if the underlying phenomena is linear.

OBJECTS OF THE INVENTION

Accordingly, it is an object of the present invention to improve the accuracy of multivariate analysis of spectral data structures derived from measurements using spectroscopy, chromatography, thermal analysis, mechanical vibration and acoustic analysis, theology, electrophoresis, image analysis, and other analytical technologies producing data of similar multivariate nature.

It is an object of the present invention to more accurately correct spectral data to reduce or eliminate multiplicative effects thereby improving and simplifying subsequent additive modeling.

To accomplish this object, it is a further object of this invention to distinguish additive features, which in spectroscopy may be chemical or physical, from multiplicative features, which in spectroscopy are generally physical, thereby reducing the danger of confusing and destroying the desired information in the multiplicative signal correction process.

It is a further object of this invention to provide error warnings if the additive (e.g. chemical) features are too similar to the multiplicative (e.g. physical) features to allow reliable multiplicative signal correction.

It is yet another object of this invention to allow for non-linear effects such as wavelength dependencies and wavelength shifts, by going from non-iterative linear to interactive non-linear modeling in the multiplicative signal correction.

It is an additional object of this invention to provide a multivariate interference rejection filter which removes the spectral information due to variable interferences without disturbing the desired analyte information.

It is still another object of this invention to integrate the multiplicative signal correction with the additive calibration regression or determination of unknown values.

It is yet another object of this invention that these additive and multiplicative correction and interference rejection filter methods provide graphically based interactive as well as fully automated operation so as to allow the users to use their judgement and experience in applying the methods if they so desire.

SUMMARY OF THE INVENTION

In accordance with the present invention, a method is used wherein spectral data of each specimen is represented by a multivariate model using previously known spectral information as opposed to only the average or "ideal specimen" spectral data utilized with simple linear regression modeling in the prior multiplicative scatter correction method. In the first instance, where the multiplicative corrections are of prime concern, the method encompasses incorporating the reference spectra of selected other components and, using multivariate estimation means rather than simple linear regression, determining the coefficients thereby resulting in substantially more accurate estimation of the magnitude of the offset and multiplicative corrections due to the reduction of the amount of unmodeled information contained in the residuals.

The present invention includes using any linear multivariate estimator to determine the correction coefficients such as multiple linear regression, generalized least squares, maximum likelihood regression, robust regression, estimated best linear predictor, partial least squares, principal component regression, Fourier regression, covariance adjustment, or non-Euclidian distance measures.

The present invention also includes using any non-linear multivariate estimation method to determine the corrections, such as linearization by Taylor expansion, the steepest descent method, Marquardt's compromise, or simplex optimization to define coefficients minimizing the sum squared error of the nonlinear model.

In addition to subtracting the offset coefficient resulting from the multivariate modeling, the present invention also comprises, as option A, using the coefficients of the interfering components derived by the linear or non-linear modeling to scale the spectra of these components so that subtraction of the scaled spectra from the data can substantially remove their contribution from the data.

The present invention also comprises, as option B, generating modified reference spectra of the interfering components that contain only those portions of the original reference spectra that are orthogonal to, and therefore uncorrelated with, one or more reference analyte spectra. The coefficients generated for these orthogonal spectra are not influenced by the presence or magnitude of analyte information contained in the raw data even if the analyte spectrum is not included in the modeling or the coefficient estimator does not inherently orthogonalize the components, so they may be a more correct representation of the magnitude of the spectral effects of the interfering components. These more accurate coefficients are then used to scale the original reference spectra prior to subtraction from the input data and the correction proceeds as in option A. This option reduces or eliminates the error in analyte spectral contribution that would otherwise be caused by subtracting an incorrect amount of a spectrum which contains some information equivalent to analyte information.

The present invention also comprises, as option C, the further scaling of the spectra of the interfering components and, if desired, the spectra of the analyte(s) so as to control the degree of spectral modification and correction applied to the data. Spectral components may be removed, downweighted, left as is, or emphasized by control of the weighting coefficients.

The present invention also comprises, as option D, updating of the analyte and interference spectra based on the results of later stages of data processing and analysis, for example based on principal components analysis (PCA) or partial least squares (PLS). This is particularly useful in conjunction with "Signal Processing Method and Apparatus" U.S. application Ser. No. 07/319,450 filed Mar. 3, 1989 by Edward Stark, one of the co-inventors of the present invention.

The present invention also comprises, as option E, interactive displaying graphical output concerning which analyte and interference spectra, if any, are causing difficulties with respect to estimation of the multiplicative correction and interactive control over which reference spectra are utilized, the spectral range included in estimating the coefficients, and the weighting of the additive corrections employed.

For a better understanding of the present invention, reference is made to the following description and accompanying drawings while the scope of the invention will be pointed out in the the appended claims.

DESCRIPTION OF THE PREFERRED EMBODIMENTS

Figure 1:
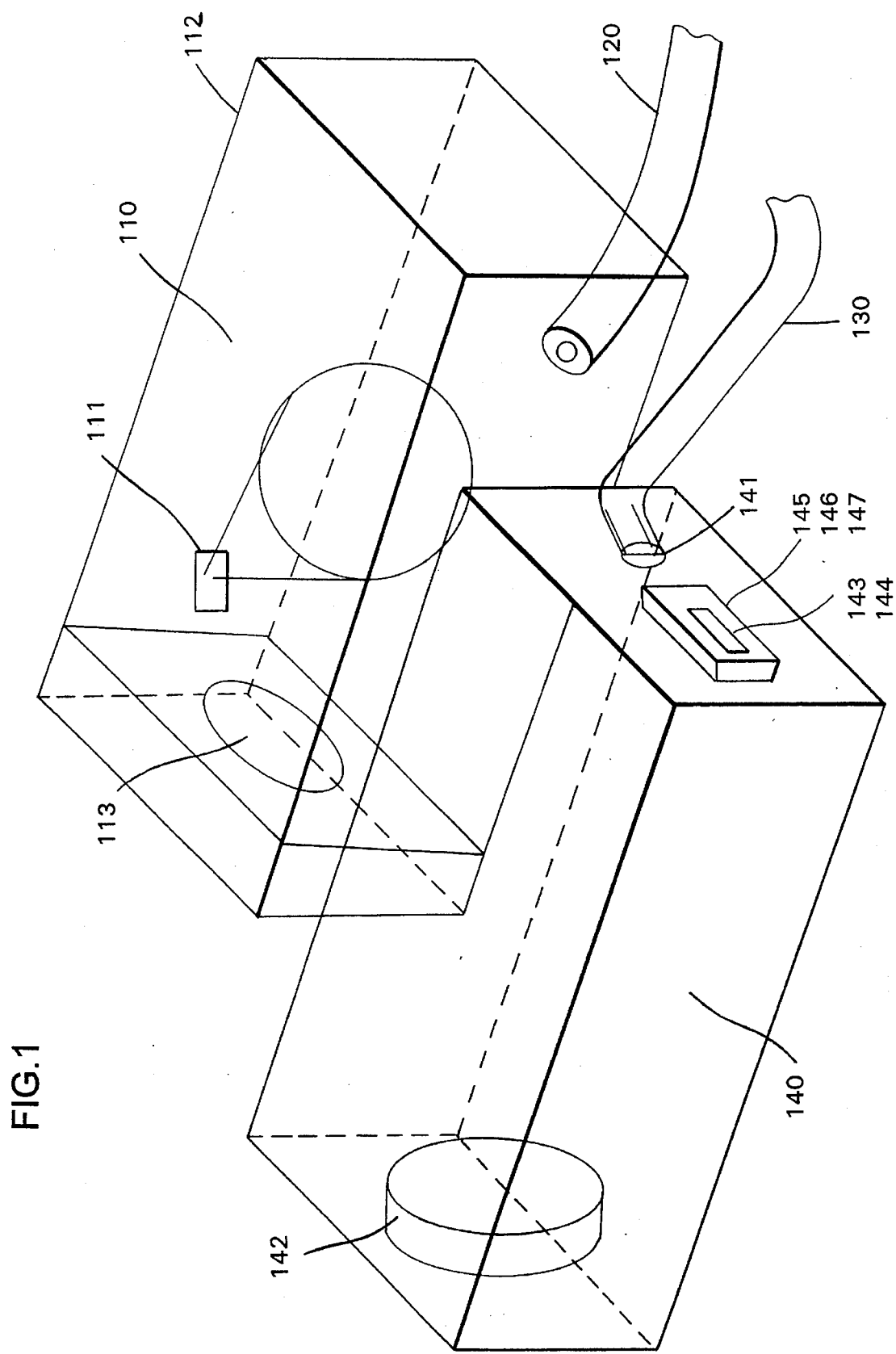
FIG. 1 is a perspective view of a spectrophotometric sensor system for use in the performance of the methods and apparatus of the present invention.

The present invention has general applicability in the field of signal and data processing, wherever "spectra" or data structures consisting of multiple interrelated data points are obtained and the variability in the data can be described as combined additive and multiplicative effects. These types of effects are common in many forms of measurement and previous efforts have bee n made to solve the problems, as discussed above.

Like Norris, the present application uses division to normalize the multiplicative variability but it employs all or most of the spectral information rather than one or a few selected wavelengths and does not depend on use of the derivative data transformation.

Like Murray and Jessiman's "mathematical ball milling" it seeks to normalize every input spectrum to some reference or "average" state by additive and multiplicative normalization, and it allows an explicit correction for wavelength effects (most simply by including wavelength as an extra additive "constituent" vector but more effectively through the use of non-linear modelling). In addition, it employs a different regressor (an actual reference spectrum, e.g. an average spectrum) for determining the multiplicative correction and it allows modeling and, if desired, subtraction of several additional phenomena at the same time.

Like the conventional Martens, Jensen, and Geladi multiplicative scatter correction (MSC), it seeks to normalize every input spectra to some reference "ideal" or "average" state by additive and multiplicative normalization, after having estimated the offset and slope parameters by some type of regression against some reference spectrum over some selected wavelength range, and this reference spectrum may be of the same kinds as those employed in MSC. However, it extends conventional MSC by explicitly modeling the effects of anticipated additive interferences and by optionally utilizing nonlinear modeling in deriving the additive and multiplicative normalization. This in turn improves the accuracy of the multiplicative correction, it allows removal of undesired interferants already at the multiplicative preprocessing stage, and it simplifies a causal understanding of the multiplicative correction and facilitates its interactive graphical optimization. It may also create interference reference spectra orthogonal to the analyte(s) spectra for use in the modeling to avoid the effects of intercorrelation between the interferant spectra and the analyte spectra which would otherwise cause inaccuracies in estimating the interferant coefficients and in the subsequent subtraction of their contribution to the spectral data being normalized.

Like the manual background subtraction, it also allows graphical interactive access, but in addition it employs statistical parameter estimation in the determination of how much to subtract. Like the general interference subtraction, it also allows modeling and subtraction of several phenomena at the same time but it combines additive and multiplicative modeling into one process mud compensates for intercorrelation among the spectral components.

If the physical situation results in a substantially linear combined additive and multiplicative structure, the measured spectral information may be considered as:

$$X_{ki}=t_{oi}+R_{ks}*t_{si}+R_{ka}*t_{ai}+R_{kj}*t_{ji}+Q_{km}*t_{mi}+e_{ki}$$

X is the spectral ordinate, e.g. absorbance, fluorescent energy, or pixel intensity or relative count, representing the measurement system response. The subscript i denotes the object or specimen while subscript k (k=1,2, . . . ,K) is the spectral variable. k may be representative of a single dimension, e.g. wavelength in optical spectroscopy, two dimensions, e.g. time and wavelength in GC-IR measurements, or more depending on the measurement technology utilized. As used here, names of matrices are capitalized (e.g. $R_{kj}$) and a matrix may comprise a single row Dr a single column of elements, for example $X_{ki}$, $Y_{ki}$, and $R_{ks}$ are individual spectra represented by single column matrices (vectors) of length K. Sets of multiple spectra form matrices (e.g. $R_{ka}$, $R_{kj}$, and $Q_{km}$). Quantities that only exist as vectors or scalers are not capitalized.

This physical situation described above is linear in the parameters, i.e. the spectral data consists of the sum of spectral components $R_{kn}$ and $Q_{km}$ that are functions of the variable k, each contributing to the spectrum of specimen i in an amount defined by the Coefficients $t_{ni}$ or $t_{mi}$, the values of which differ from specimen to specimen but are not functions of k. $e_{ki}$ is additive random error in the spectral data. The spectral components may be considered the fundamental signatures of the underlying chemical or physical parameters being measured while the coefficients relate to the quantity of the parameter and the sensitivity of the measurement. Many fundamental physical processes generate such linear spectral data, e.g. the absorbance spectra of chemical mixtures measured by optical spectroscopy. $t_{oi}$ describes a additive offset and any additive baseline that is a function of k can be considered an additional spectral component $Q_{km}$. Variations in the additive offset and the sensitivity of the measurement among data from different specimens contributes the additive and multiplicative errors for which this invention provides improved data corrections.

The fundamental improved method of data normalization provided by this invention is based on the use of previously obtained reference spectra $R_{ks}$, $R_{ka}$, and $R_{kj}$ to model the input spectral data $X_{ki}$. Therefore, they are separately considered in the equation above. $Q_{km}$ describes spectral information present in the input data that is not represented by any of the reference spectra. The objective is to include sufficient spectral information in $R_{ks}$, $R_{ka}$ and $R_{kj}$ so that $Q_{km}*t_{mi}$ is small enough that it may be safely neglected.

$R_{ks}$ is the primary "standard" spectrum used as the basis for determining the multiplicative correction coefficient. Typically, it represents the average spectrum of the class of specimens, the spectrum of the solvent within which the analyte is dissolved and to which the analyte concentration is referenced (e.g. molality), or the spectrum of a naturally occurring or artificially introduced tracer material. On the basis that the offset $t_{oi}$ is an artifact that should be removed, and that it is desired to normalize the coefficients of each spectrum so that the standard component $R_{ks}$ always has the same contribution in the data, a corrected spectrum $Y_{ki}$ can be defined as $$Y_{ki}=(X_{ki}-t_{oi})/t_{si}.$$

In order to perform such a correction, the values of $t_{oi}$ and $t_{si}$ must be derived from the data $X_{ki}$ separately for each specimen i. Improved methods and apparatus for estimating these values are the subject of this invention.

$R_{ka}$ are ore or more reference spectra representing the expected influence of the analytes of interest on the input data. In this context analyte is used broadly to indicate the quality sought in the subsequent analysis of the data, for example a quantity of a constituent or an identification of the specimen or one or more of its components based on a between-class discriminant function. $R_{kj}$ are reference spectra representing the expected influence of various undesired interferences, whether chemical or physical interferences in the specimen or artifacts introduced by the instrumentation, on the input data $X_{ki}$.

If $R_{ks}$ is the ideal spectrum e.g. the average taken under the same measurement conditions, the expected value of $t_{si}$ is 1. If $R_{ks}$ is a pure solvent taken under the same conditions, $t_{si}$ is expected to be less than 1, depending on solute concentration. If $R_{ks}$ is taken under different pathlength or concentration conditions, $t_{si}$ can be less than or greater than 1. $t_{ai}$ and $t_{ji}$ are related to the concentration of the components and differences in the measurement sensitivity between the data for $R_{kn}$ and that for $X_{ki}$.

The reference spectra represent previously known more or less accurate information about how the qualities sought in the subsequent analysis (e.g. analyte concentrations or between-class discriminant functions) and various interferences are expected to affect the input data. These reference spectra can be based on direct physical measurements of individual specimens, direct physical measurement of the separate constituents, or statistical summaries or estimates of the spectra based on Sets of specimens. For example, $R_{ks}$ may be the average of all the spectra obtained by measurement of the calibration set of specimens or the result of a careful measurement of a solvent blank. It is desireable that the spectral characteristics of $R_{ks}$ be stable. If $R_{ks}$ is the average spectrum, this implies use of a reasonably large number of representative individual spectra in computing the average spectrum. In the case of a solvent spectrum $R_{ks}$, it is often desireable to characterize the solvent by more than one spectrum to encompass possible variations due to, for example, the influence of specimen composition, temperature or other environmental factors. The most stable spectral component is then used as $R_{ks}$ and the spectra representing deviations or variations in the solvent spectrum are included in $R_{kj}$.

The $R_{ka}$ and $R_{kj}$ reference spectra are often statistical estimates extracted from the measured data from sets of specimens, although directly measured spectra are also useful in many cases. Honig's spectral reconstruction (D. E. Honigs, G. M. Hieftje, and T. Hirschfeld, A New Method for Obtaining Individual Component Spectra from Those of Complex Mixtures, Applied Spectroscopy, 38(3), pp. 317–322, a copy of which being annexed hereto) provides a method for extracting spectra from a set of mixture specimens based on knowledge of the concentration values. Principal component analysis (PCA) and partial least squares (PLS) provide orthogonal sets of spectra representative of the variation in the data. Stark's method (U.S. patent application Ser. No. 07/319,450) provides reference spectra for previously unknown variations based On analysis of replicate data. In the simplest operation of the present invention, i.e. correction for offset and multiplicative factors, the primary requirement of $R_{ka}$ and $R_{kj}$ is that they reasonably span the variation of $X_{ki}$ so as to stabilize the modeling and spectral accuracy and specificity are not essential. For the more complex options, in which $R_{ka}$ and $R_{kj}$ are incorporated into the output data as corrections, the quality of $R_{ka}$ and $R_{kj}$ become more important. The accuracy and specificity of the $R_{ka}$ spectral data is particularly important in orthogonalization of $R_{kj}$ either explicitly or implicitly and when used for added weight as described below. The spectral information in $R_{ka}$ and $R_{kj}$ may be represented in various ways with respect to redundancy and collinearity, for example one individual vector for each phenomenon, several replicates or specimens, statistical summaries (averages, bilinear components, square root of covariance matrices, etc.), or rotated representations where some or all collinearities have been eliminated. In a preferred embodiment, redundancy is eliminated by averaging so that the number of vectors equals the number of phenomena being modeled.

An intrinsically nonlinear data structure may arise because the physics of the measurement and/or instrumentation has introduced characteristics differing from those described above. One common type of nonlinearity is analytical sensitivity (e.g. gain, pathlength) which is a function of the variables. A more general description of the input data then takes the form $$\begin{aligned} X_{ki} &= C_{ki} + D_{ki}[t_{oi} + R_{ks}*t_{si} + R_{ka}*t_{ai} + R_{kj}*t_{ji}] + e_{ki} \\ &= C_{ki} + D_{ki}[R_{kn}*t_{ni}] \end{aligned}$$

This describes a structure resulting from nonlinear distortions of the, fundamentally linear structure described by $[R_{kn}*t_{ni}]$ where $$R_{kn}=[1,R_{ks},R_{ka},R_{kj}]$$

and any other spectral data, for example the $Q_{km}*t_{mi}$, are included in the error $e_{ki}$. It will be appreciated by those skilled in the art that other forms of nonlinearity may arise which can also be described as distortions of the basic linear structure above.

In the present case, $C_{ki}$ and $D_{ki}$ may each be a function of the spectral value $X_{ki}$, of the wavelength k, or of both. In the usual nonlinear case of small but significant deviations from linearity, the values of $C_{ki}$ and $D_{ki}$ are will be close to 0 and 1 respectively. If the nonlinearity is negligible, $C_{ki}$ can be set equal to 0 and $D_{ki}$ equal to 1. The resulting structure is then equivalent to the linear additive and multiplicative structure discussed above.

The form of $C_{ki}$ and $D_{ki}$ are related to the causes of nonlinear behavior. For example, in spectroscopy the amount of scattering and therefore the effective pathlength may vary as a smooth function Of wavelength. Refractive index effects have similar smoothly varying forms with respect to wavelength. Therefore, $D_{ki}$ may be a smooth but non-linear function of wavelength. On the other hand, the effective pathlength may be a smooth function of absorbance, as in convergence error in transmission spectroscopy, where an increase in reduces the energy from longer pathlengths more than from shorter ones, thereby making the effective pathlength grow shorter as absorbance increases. Measurements in transflection mode, where convergence error is maximized, resulted in use of a model that gave excellent correction $$X \text{ corrected} = b_0 + X*b_1 + X^3*b_3$$

where X is measured log(1/R). In general both k and X variables should be included in the nonlinear model, for example in transflection of scattering samples.

For generality, the scattering pathlength and similar multiplicative effects can be described as a function of k in accordance with the series expansion $$D_{ki} = d_{0i} + d_{1i}*k + d_{2i}*k^2 + d_{3i}*k^3 +$$

Again for generality, convergence error and other effects that affect the linearity of the value of X can be described by $$X_{ki} \text{ real} = c_{0i} + c_{1i}*X_{ki} + c_{2i}*X_{ki}^2 + c_{3i}*X_{ki}^3 +$$

Therefore, a general form for $C_{ki}$ and $D_{ki}$ can be described as a product of these series, ie a new series in terms of the powers of k and X and their cross products, removing redundant constants and terms in k or X and normalizing so that the linear magnitude information is kept in $[R_{kn}*t_{ni}]$ and $C_{ki}$ and $D_{ki}$ carry only the information relating to the nonlinearity. $C_{ki}$ and $D_{ki}$ are matrices containing k rows, and as many columns as required for the number of terms in the appropriate power series approximations.

It is the underlying intrinsically linear additive structure that is desired for later analysis steps using linear multivariate calibration, validation and determination procedures. Therefore, the corrected spectra $Y_{ki}$ are formed by $$\begin{aligned} Y_{ki} &= \{(X_{ki} - C_{ki})/D_{ki} - b_{oi}\}/b_{si} \\ &= [R_{ks} + R_{ka}*b_{ai} + R_{kj}*b_{ji}] + e_{ki} \end{aligned}$$

where the $b_{ni}$ are estimates of the true $t_{ni}$ and $C_{ki}$, $D_{ki}$, and $b_{ni}$ are derived from the data $X_{ki}$.

The corrected spectrum $Y_{ki}$ comprises the standard spectrum $R_{ks}$ and linear additive deviations from $R_{ks}$ caused by analytes, interferants, and errors, and it is therefore suitable for further linear data analysis.

Preferred embodiments of the above are illustrated in the figures and further described below. In FIG. 1 for instance a photospectrophotometric sensor system 100 as used in the present invention is described. This system can be used, for example, in the determination of analytes in blood or, for instance, in the display of glucose levels in blood. This sensor system 100 comprises an optical source 110, for example a General Electric type EPT tungsten halogen projection lamp 111 mounted in a housing 112 containing a fan 113 for cooling and coupled to a 1 cm. diameter fiber optic bundle 120 for transmitting energy to the specimen, e.g. the surface of the skin of a patient. Energy transmitted through the tissue is collected by a second fiber optic bundle 130, which transmits it to the spectrophotometer 140. This spectrophotometer comprises an entrance slit 141, a concave holographic grating 142, and one or more diode array detectors 143 and their order sorting filters 144, arranged to measure energy at different points in the spectral image formed by the holographic grating, and therefore at different wavelengths within the visible and near-infrared regions of the electromagnetic spectrum. Each detector channel has an associated preamplifier 145, the output of which is multiplexed by multiplexer 146 into a programmable gain and offset amplifier 147. The spectrophotometer 140 is further described in "Improved Grating Spectrometer", a U.S. patent application filed Aug. 24, 1989 by Edward Stark, one of the coinventors of the present invention. The application has issued on Mar. 5, 1991 U.S. Pat. No. 4,997,281. The contents of said patent are incorporated herein by reference.

Figure 2:
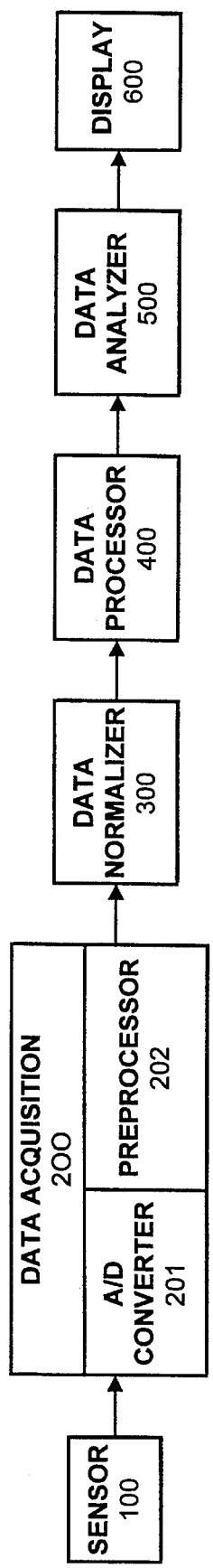
FIG. 2 is a general block diagram of the apparatuses used as components in conjunction with the present invention as shown in FIG. 1.

As is shown in FIG. 2, the time sequential multiplexed analog signal is then converted to digital form by an analog to digital converter 201 in data acquisition system 200. In preprocessor 202, the energy data is processed to eliminate instrumental offsets and to reduce both systematic and random noise and then ratioed to obtain data relating to transmission of the specimen. This data is then linearized with respect to the analyte information of interest, e.g., the logarithm of transmission is more or less linear with concentration of chemical constituents within the specimen. The data is then in form to be normalized in accordance with the methods of this invention. Although the details may differ, similar functions are utilized in obtaining spectral data of the other forms discussed above.

The additive and multiplicative corrections of this invention are performed by data normalizer 300, which comprises special purpose digital computation logic. After normalization, the data may be further processed in processor 400 prior to use for multivariate calibration, validation and determination of unknown values. For example, processor 400 may comprise the invention of "Signal Processing Method and Apparatus" U.S. patent application Ser. No. 07/319,450 filed Mar. 3, 1989. The contents of said application are incoporated herein by reference. Finally, the data is analyzed in the data analyzer 500 which performs the functions of multivariate calibration, validation, and determination required to generate the analytical values then presented on display 600.

Figure 3:
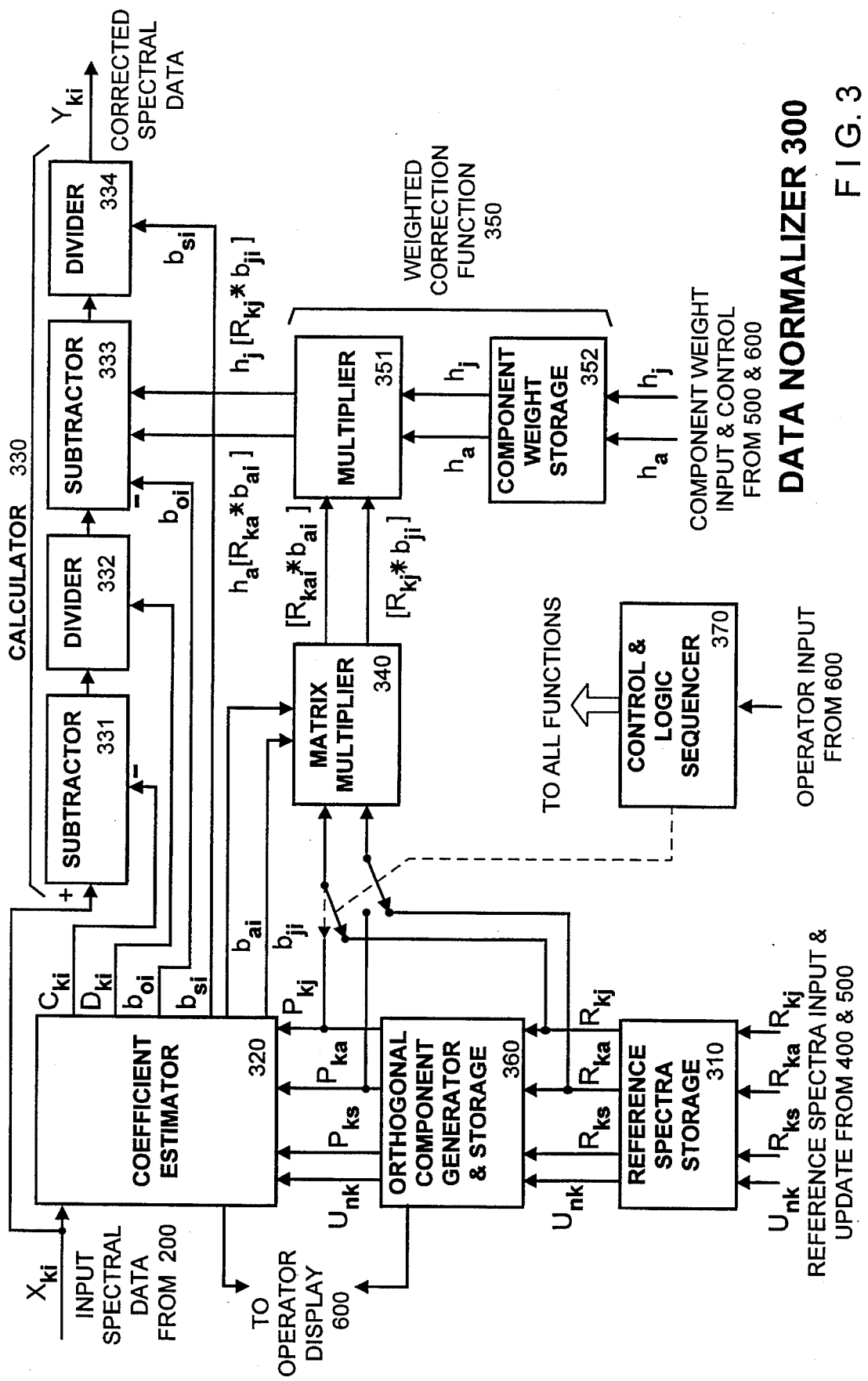
FIG. 3 is a block diagram of the data normalizer unit as used in the present invention.

The data normalizer 300 of the present system illustrated in FIG. 3 provides a number of options for processing the input spectral data $X_{ki}$. The basic improved method of data normalization provided by this invention is based on the use of reference spectra $R_{ks}$, $R_{ka}$, and $R_{kj}$ stored in the reference spectra storage 310 to model the input spectral data $X_{ki}$ by means of the coefficient estimator 320, and to determine corrected spectral data $Y_{ki}$ by means of calculator 330. Functions 340, 350, and 360 provide additional options which are bypassed for the basic corrections. The control and logic sequencer 370 provides the timing, data selection, and control signals required to perform the selected functions in proper sequence.

In a preferred embodiment shown in FIG. 3, this correction is implemented by the calculator function 330 comprising subtractor 331, divider 332, subtractor 333, and divider 334 that perform successive operations on $X_{ki}$ involving the coefficients $C_{ki}$, $D_{ki}$, $b_{oi}$, and $b_{si}$ generated by the coefficient estimator 320. These operations are performed sequentially element by element by indexing k with a first counter and performing the required sequence of digital arithmetic functions under logic control based on the state of a second counter. These digital arithmetic functions are available digital logic functions utilized in computers, and may conveniently be obtained in the 80287 math coprocessor device or an array processor.

In a preferred addition to the basic preferred embodiment described above and shown in FIG. 3, additional correction spectra $[R_{ka}*b_{ai}]$ and $[R_{ki}*b_{ji}]$ are formed by matrix multiplier 340 from the reference spectra and their associated coefficients that were also generated in coefficient estimator 320. A matrix multiplier to form the spectrum $[R_{kn}*b_{ni}]$ for a single input spectrum i, consists of short term storage for the both inputs, a multiplication and summation circuit, an address sequencer which accesses the corresponding elements n of $R_{kn}$ and $B_{nk}$ and a second address sequencer which accesses the rows k of $R_{kn}$ and addresses the short term storage which keeps the resulting k×1 matrix. Matrix multiplication is also a standard function of available array processors. This additional combined correction spectrum may be used directly by subtractor 333 to further correct $Y_{ki}$, which becomes $$Y_{ki} = \{(X_{ki} - C_{ki})/D_{ki} - b_{oi}\}/b_{si} - [R_{kj}*b_{ji}] = [R_{ks} + R_{ka}*b_{ai}] + e_{ki}$$

Here the $[R_{ka}*b_{ai}]$ represents the analyte(s) of interest, which must not be removed. Ideally, for a single analyte, $[Y_{ki} - R_{ks}]$ is simply the analyte spectrum whose scale factor represents the amount of analyte present.

Often, only a subset of the possible $[R_{kj}*b_{ji}]$ corrections are applied at this stage of data processing, because later additive linear modeling may be more effective than the spectral subtraction based on previously known reference spectra performed here. The $[R_{kj}*b_{ji}]$ should include, however, those interferants that are difficult or impossible to adequately represent in the calibration data, e.g. moisture and temperature as previously discussed.

Greater control of the situation is provided in a preferred embodiment that also incorporates multiplier 351 and component weight storage 352. In this embodiment, the amount or weight ha or hj of each correction spectrum that is subtracted in forming $Y_{ki}$ can be controlled by the operator or in accordance with information obtained in later data processing steps. The corrections then become $ha[R_{ka}*b_{ai}]$ and $hj[R_{kj}*b_{ji}]$. The corrected spectrum then becomes $$Y_{ki} = \{(X_{ki} - C_{ki})/D_{ki} - b_{oi}\}/b_{si} - hj[R_{kj}*b_{ji}] - ha[R_{ka}*b_{ai}]$$
$$= R_{ks} + (1-hj)[R_{ka}*b_{ai}] + (1-ha)[R_{ka}*b_{ai}] + e_{ki}$$

A weight of hj=1 is used when complete cancellation is desired, while a weight of hj=0 provides no correction for interferant j and ha=0 preserves the analyte signal unchanged. Values 0<hj<1 may be used to downweight information that has uncertainty or potentially harmful effects on later data analysis without total rejection. ha<0 increases the weight of the analyte information, thereby reducing the relative importance of other information in the corrected signal.

The orthogonal component generator 360 provides for transformation of the reference spectra $[R_{ks}, R_{ka}, R_{kj}]$ into a new set of spectra, $[P_{ks}, P_{ka}, P_{kj}]$, some or all of which are orthogonal to each other. If the reference spectra are latent variables derived from a single PCA or PLS analysis, they are orthogonal by definition. If they are measured spectra of components or otherwise separately derived, they will generally be intercorrelated, which if severe enough may cause errors in the coefficient values or failure of the coefficient estimator to complete its operation. If orthogonal reference spectra are created, new reference spectra may be added without requiring complete recalculation by the coefficient estimator. Orthogonal reference spectra also minimize the number of operations required by the coefficient estimator to determine the coefficients.

In a preferred embodiment, the orthogonal component generator performs a Gram-Schmidt orthogonalization in accordance with $$Z_i T = (I - Z(Z'Z) - 1Z')Z_i$$
$$= Z_i - Z(Z'Z) - 1Z'Z_i$$

where

I = the identity matrix

Z = the matrix of vectors already transformed, $Z_i$ = the column vector of X to be transformed, and $Z_i T$ = transformed vector orthogonal to vectors already in Z.

Z' = transpose of Z, $[\ ]^{-1}$ = inverse of $[\ ]$

Z comprises orthogonal columns therefore [Z'Z] is diagonal of size (i)×(i) and determining $[Z'Z]^{-1}$ is trivial by inversion of the individual elements.

The first reference spectrum to be orthogonalized is $R_{ks}$ (i=2, Z'Z=K from column of 1's) whereby $$P_{ks} = R_{ks} - (\text{Sum } R_{ks})/k = R_{ks} - \text{average } R_{ks}.$$

The variations of $R_{ks}$ are preserved in $P_{ks}$, therefore the coefficient bs is not affected by the orthogonalization. Each succeeding $R_{kn}$ is then orthogonalized against the matrix formed by the preceding orthogonal $P_{kn}$ spectra, until all reference spectra are orthogonalized into matrix $P_{kn} = [1, P_{ks}, P_{ka}, P_{kj}]$. Each spectrum $P_{kn}$ comprises the residuals of the regression of $R_{kn}$ on the preceding orthogonal $P_{kn}$. If a spectrum $P_{kn}$ is 0 or has only small values, it provides warning of dependence between spectra that could cause problems in coefficient estimation. In such case, the information is provided to the operator, or separate decision circuitry, to determine whether to delete the spectrum from the model, to downweight its importance, or to accept it without change. Orthogonalization processing may be performed solely for the purpose of generating this warning information. When full orthogonalization is chosen, the reference spectra input to matrix multiplier 340 are the $P_{kj}$ and $P_{ka}$.

The orthogonal component generator and storage 360 comprises storage for $P_{kn}$, the portion that is filled as the process proceeds comprising Z, storage for [Z'Z]−1, storage for the intermediate product Z(Z'Z)−1, storage for $Z_i$, storage for the intermediate product $Z'Z_i$, point by point multiply and sum logic, scalar inversion (1/a) logic, a subtractor, and the sequencer to select data from storage for processing, to control the processing sequence, and to direct storage of results. Circuit devices to perform these functions include the Intel 80287 math coprocessor for hardware implementation of the arithmetic functions, CMOS static ram chips (e.g. 4 parallel Motorola MCM6226-30 128K×8) to provide 32 bit resolution in storage of the digital data, and standard programmable array logic devices (PAL's) combined with a clock and counter as the sequencer. Each matrix element is acted on in sequence in accordance with the hardware logic. The required functions can also be obtained with a standard array processor operated in sequential fashion by the sequencer.

Operation is as follows after clearing to 0's:

1. Set n and the first column of the $P_{kn}$ storage to 1's. (Z=Pk1)

2. Set the first element of [Z'Z]−1=1/K

3. Set all elements of Z[Z'Z]−1=1/K

4. Increment n

5. Move spectrum $R_{kn}$ to $Z_i$ storage ($R_{ks}$ for n=2) (K×1)

6. Multiply and sum to form $Z'Z_i$ (n−1×1)

7. Multiply and sum to form an element of Z[Z'Z]−1Z'$Z_i$ (K×n−1)

8. Subtract sum from the same element of $Z_i$
9. Store in that element of column n of $P_{kn}$ storage (K×n)
10. Repeat 7–10 for K points in spectrum $R_{kn}$ to get $P_{kn}$ (Z=Pk1 ... $P_{kn}$)
11. Multiply and sum to form $Z_i'Z_i$ (scaler)
12. Invert (1/a) and store in nth element of $[Z'Z]^{-1}$ (n×n)
13. Multiply and to form new elements of $Z[Z'Z]^{-1}$ (K×n)
14. Repeat from step 4 until all $R_{kn}$ are used. (Z=$P_{k1}$ ... $P_{kN}$) (K×N)
15. End The contents of $Z[Z'Z]_{-1}$ is the transpose U' of U=[Z'Z]$-1Z'$ which is useful in finding multiple linear regression coefficients by matrix multiplication.

Full orthogonalization may modify the spectra so drastically that it becomes difficult to recognize their origin and the associated coefficients are thoroughly aliased compared to the original quantities represented by the reference spectra. This is particularly troublesome when interference subtraction, interference downweighting, or analyte enhancement is desired. These factors often make it desireable to perform less drastic processing.

An alternative preferred embodiment orthogonalizes each interferant spectrum only against the analyte spectrum by the simple linear regression model, $$R_{kn}=b_{on}+R_{ka}*b_{an}+e_{kn}; \ P_{kn}=R_{kn}-b_{on}-b_{an}*R_{ka}$$

With this procedure, $R_{ka}$ may be omitted in the estimation of the $b_{kj}$ coefficients without causing errors in their determination. This method has the advantage of only removing analyte related information from the reference spectra, thus the analyte spectrum is unaffected, the interferant spectral shapes are minimally affected, and the coefficients have physical interpretations. In this case, the correct input to the matrix multiplier 340 is $R_{kj}$ rather than $P_{kj}$, to properly subtract the portion of $R_{kj}$ correlated with $R_{ka}$. Implementation of this digital logic requires only a subset of the functions described previously.

If even this degree of reference spectrum modification is undesireable, the orthogonal component generation is bypassed and the original reference spectra are passed to the coefficient estimator.

The coefficient estimator 320 mathematically determines the coefficients applicable to the various components used to model the input data. In general, the coefficient estimation process involves creating a model representative of the input spectral data that is a function of the reference spectral data and, in nonlinear models, of other variables such as the input spectral data itself and k.

In the linear case, taking $R_{kn}=[1,R_{ks},R_{ka},R_{kj}]$, a matrix where each row represents observations at a value k of the spectral variable and each column is a reference spectrum $R_{kn}$ incorporated in the model, coefficient estimator 320 fits $X_{ki}$ to Rnk by some method, minimizing the residuals $e_{ki}$ in $$X_{ki}=b_{oi}+R_{ks}*b_{si}+R_{ka}b_{ai}+R_{kj}*b_{ji}+e_{ki}.$$

Methods for achieving this linear modeling include generalized least squares, maximum likelihood regression, robust regression, estimated best linear predictor, partial least squares, principal component regression, Fourier regression, covariance adjustment, and others. For example, generalized least squares with generalized inverse models $X_{ki}$ by $$X_{ki}=R_{kn}*b_{ni}+ei \text{ where } b_{ni} \text{ is } [b_{oi},b_{si},b_{ai},b_{ji}] \text{ calculated by}$$

$$b_{ni}=[R'V(i)^{-1}R]^{\sim}R'V(i)^{-1}X_{ki}$$

where $[ \ ]^{\sim}$ means a generalized inverse and where covariance matrix v(i) can be iteratively updated based on the previous fit for this specimen i.

However, a preferred embodiment uses the more usual linear modeling performed by multiple linear regression where $$b_{ni}=[R'R]^{-1}R'X_{ki}.$$

When the specific $R_{kn}$ a to be used are known in advance, $$U_{nk}=[R'R]^{-1}R'$$

can be precomputed externally and stored with the reference spectra, thereby minimizing the requirements on the data normalizer 300. If full rank Gram-Schmidt orthogonalization is used, $U_{nk}$ is available from that process. In either case the calculation of the coefficients of the linear model involves a simple matrix multiplication. A matrix multiplier for $U_{nk}$ and $X_{ki}$ consists of short term storage for one or both inputs, a multiplication and summation circuit, an address sequencer which accesses the corresponding elements k of $U_{nk}$ and $X_{ki}$ and a second address sequencer which accesses the rows n of $U_{nk}$ and addresses the short term storage which keeps the resulting $b_{ni}$ values. In the more general case of multiple linear regression, matrix [R'R] must be formed and inverted to obtain $[R'R]^{-1}$ prior to matrix multiplication by R' to obtain $U_{nk}$. This function can readily be accomplished with an available array processor and suitable logic sequencer.

A second preferred embodiment of the coefficient estimator which avoids matrix inversion is a principal components regression (PCR) device, which requires no pretreatment of $R_{kn}$ and no matrix inversion.

In the case of nonlinear modeling, the coefficient estimator 320 becomes more complex as each nonlinear coefficient becomes a vector of length k. $C_{ki}$ and $D_{ki}$ are therefore matrices containing a number of coefficient vectors that depends on the form of the nonlinear model.

These coefficients can not be determined by multiple linear regression or other bilinear methods so an interactive procedure must be used. Methods in the literature include linearization by Taylor series, steepest descent Marquardt's compromise, and simplex optimization: (N. Draper and H. Smith, Applied Regression Analysis, Second Edition, John Wiley & Sons, New York 1981 pp. 458–465).

Figure 4:
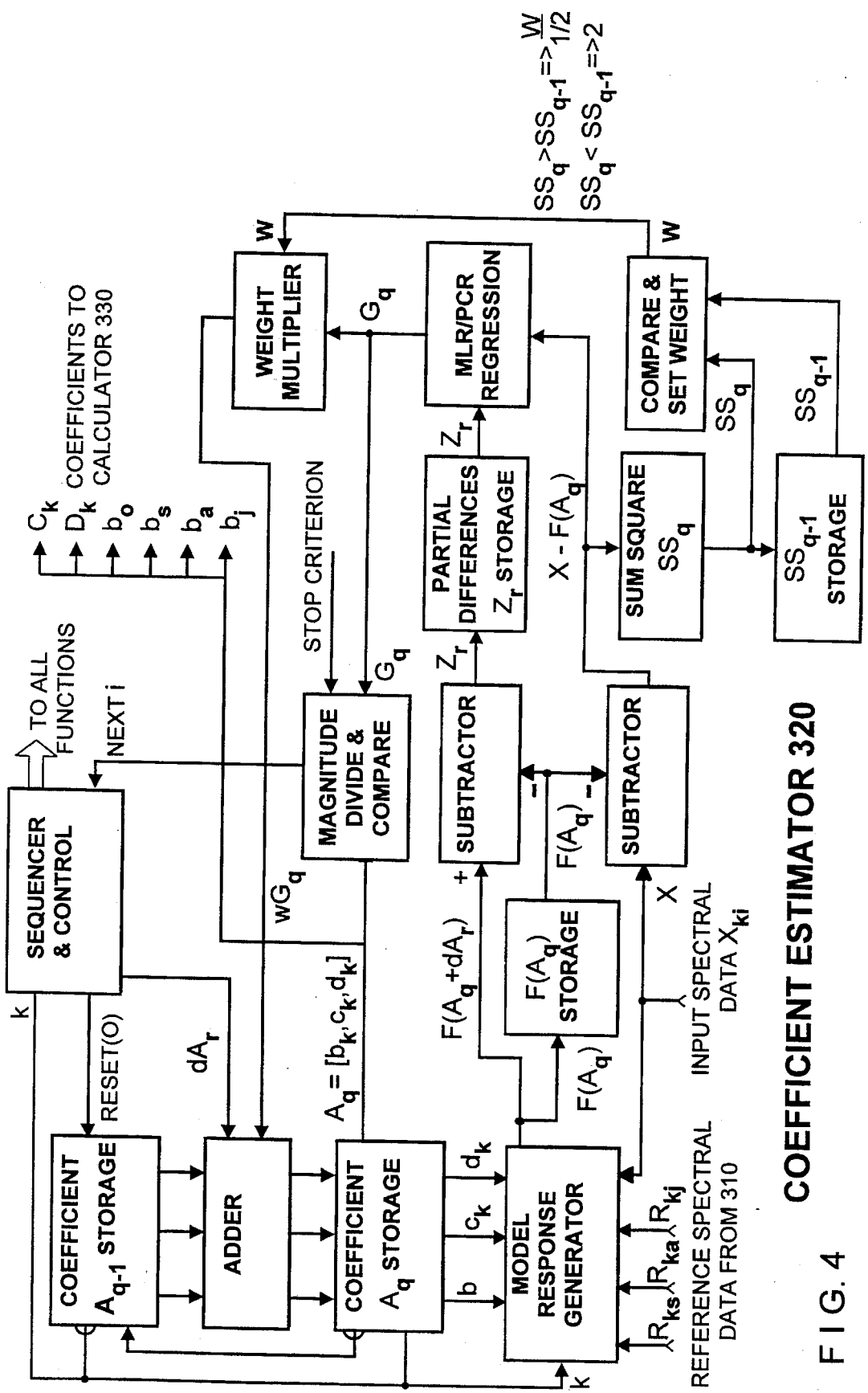
FIG. 4 is a block diagram of a non-linear model coefficient estimator used in conjunction with the present invention.

A preferred embodiment uses the coefficient estimator 320 illustrated in FIG. 4 which employs Taylor series linearization. The model response generator 321 calculates the vector F from the reference spectra Rkn, the present value Ari of the coefficients being generated by the iterative process, the variable k and the input spectral data Xki. This operation involves matrix multiplication and summation in accordance with the appropriate form of model as discussed above. The set of coefficients Ari, comprising cni of Cki, dni of Dki, and bni, are initially stored in coefficient Aq–1 storage 322a. They may be modified by means of adder 322b through addition of a weighted correction wGq or of increment dAr to one of the coefficients at a time to create the present values stored in coefficient Aq storage 322c and used by model response generator 321. The remaining functions will become obvious from the following description of the operation.

1. Initialize A(q–1), k, F(Aq), and iteration counter q to 0;
2. Load Rkn into the partial differences Zr storage 323b;
3. Regress Xki on Rkn to determine the linear model bni;

4. Set w=1 and add bni to A(q−1) to put bni in Aq storage 322i c;
5. Set dOi=1 in Aq and generate F(AO), store in 323c;
6. Transfer Aq from 322c to A(q−1) storage 322a;
7. Sequentially increment Aq values by adding dAr by 322b;
8. Calculate F(Aq+dAr) and subtract F(Aq) to get Zr;
9. Store in Zr and iterate 7, 8, 9 for all r;
10. Form X-F(Aq) and regress on Zr using 324 to form Gq;
11. Compute SSq, compare to prior value, and select weight by 326;
12. Added weighted Gq to A(q−1) to form next Aq;
13. Compare Gq/Aq with stop criterion, if greater next q, else end.

This operation is controlled by sequencer 327.

It should be obvious to those of ordinary skill in the art that some of the above operations may be performed in different order without significantly affecting the results obtained. It should also be obvious that the functions shown can [(be?)] be implemented with common digital logic circuits well understood by those of ordinary skill or by available microcode controlled array processors, such as the Data Translation Model DT7020 with the MACH DSP Subroutine Library of microcode. Copies of the applicable Data Translation 1988/[99 (89?)] 89 Data Acquisition Handbook pages have been annexed hereto and incorporated in their entirety by reference.

One variation in the method used to estimate and correct for multiplicative effects is to fit an additive model and a multiplicative model in an interactive sequential fashion.

1. Let $X=(x_{ik})$ be the matrix of spectral ordinates for i=1,2, ... N objects, k=1,2, ... ,K wavelengths. The multiplicative effect is modeled from the spectral data using a standard multiplicative scatter correction (i.e., avoiding the use of components for practicing the present invention) yielding the corrected spectral data Z.

2. Estimate an additive model:

$$Z=1*z_{mean}+D*P'+E$$

where 1 is a vector of ones of size k, $z_{mean}$ is the mean vector of Z, and $P=(P_{kl})$ spans the spectral variations of analytes and interferences as well as possible and/or to the extent the user wishes. P may include any of the following: input component spectra, estimated component spectra, loadings from a PCA or PLS analysis of residuals after fitting estimated component spectra, or loadings from PCA or PLS analysis of X or Z. D represents the associated vector of weights obtained by PCA or PLS, for example.

3. Reconstruct the spectral data without the estimated additive effects, $$Y=X-D*P'$$

4. Estimate the multiplicative effects on Y using one of the methods proposed in this invention.

5. Construct a new matrix of corrected spectra Z from X and repeat step 2, step 3, and step 4 until convergence occurs.

6. Following performance of steps 1–5, the finally corrected spectra, Z, may be used as a multiplicative corrected input spectra or from this finally corrected spectra, Z, the desired D and P factors which one wants to take away may be subtracted.

In this method, the multiplicative effects, say from a physical model, and the additive effects, say from a chemical model, are obtained at separate steps in the process. However, the results of each model are adjusted for the effect of the other model. That is, the results are adjusted for the multiplicative effects and the additive and interferent effects present in the bilinear factors which are chosen for elimination. In addition, this technique allows for a wide variety of choices of kinds of components to include in the chemical model varying from known interferents and component spectra through statistically estimated PCA or PLS factors.

The fundamental improved method of data normalization provided by this invention is based on the use of previously obtained analyte and reference spectra to model multiplicative effects on spectral data, although use of the invention does not specifically require the estimation of multiplicative effects directly from the input spectral data using said reference spectra. Rather, the multiplicative effects can be modeled from coefficients and/or loadings derived from statistical analyses (e.g. multiple linear regression, principal component analysis, partial least squares, and generalized least squares) of spectral data. The multiplicative effects obtained in this way can be used to correct the spectral data for multiplicative effects.

For example, if the physical situation results in a combined additives and multiplicative structure, the measured spectral information may be considered as $$X=T*P'+E$$

where $X=(x_{ik})$ is the matrix of spectral ordinates for i=1,2, ... N objects, k=1,2, ... ,K wavelengths, $T=(t_{il})$ is the matrix of scores for objects i, bilinear factors l1=1,2, ... ,L obtained from some bilinear model (e.g. principal component analysis, partial least squares, etc.), $P=(p_{kl})$ are the loadings for objects i on bilinear factors l, and $E=(e_{ik})$ are the residuals between data X and model T*P'. The loadings P can then be decomposed into a function of a reference spectra $r=(r_k)$ (e.g. the Bean of the X data) and a matrix $G=(g_{km})$ spanning the spectra for analyte and interference phenomena m=1,2, ... ,M:

$$P'=d*r'+h*1'+C*G'+F$$

where $d=(d_l)$ and $h=(h_l)$ are vectors of length L, 1 is a vector of ones of length K, $C=(c_{lm})$ is a matrix of regression coefficients of size L×M which quantifies the analyte and interference contributions, and $F=(f_{1k})$ contains the residual loadings with the multiplicative, analyte, and interference phenomena removed. d, h, and C can be estimated by regression of P' on r, 1, and G by some method (e.g. weighted least squares). C*G' could be reduced in size by elimination of effects if the relative size of the chemical or interferent effects are small The additive and multiplicative effects for the input spectra can be obtained from the loadings and scores by $$a=T*h \text{ and}$$

$$b=T*d$$

If the mean values of vectors a and b are $a_{mean}$ and $b_{mean}$, respectively, the input spectra, corrected for additive and multiplicative effects, can be determined by $$Y_i=[X_i+a_{mean}-a_i]*b_{mean}/b_i$$

The quantities $(a_{mean}-a_i)$ and $(b_{mean}/b_i)$ appear in the equation to scale the corrected spectra such that the individual spectrum's additive and multiplicative corrections are made relative to the overall additive and multiplicative effects.

In addition, the input spectral data can be corrected simultaneously for interferent contributions and additive and multiplicative effects, $$Y_i = [X_i - T*C^{*}*G^{*'} - a_i + a_{mean}] * b_{mean}/b_i$$

$C^*$ and $G^*$ are user-chosen subsets of C and G which include those interferents and analytes of interest which it is desired to eliminate from the input spectral data. The corrected spectrum $Y_i$ represents the original input spectra after correction for the additive, multiplicative, and interferent effects present in the bilinear factors.

A modification to the above technique includes the method whereby the additive, multiplicative and interferent effects are modeled from the coefficients and/or loadings of multivariate statistical techniques and the corrections are applied directly to the multivariate scores rather than to the input spectral data.

Using the prior example where the input spectral data X are modeled using a bilinear model, $$X = T*P' + E$$

the offset-corrected and interferent-corrected spectral data can be defined as $Z = (z_{ik})$ where $$Z = X - T*h*b \; 1' - T*C^{*}*G^{*'} = T*(P' - h*l' - C^{*}*G^{*'}) + E$$

where T, h, 1, P, $C^*$ and $G^*$ are defined as above. Z represents a general case. More specifically, Z can be corrected for offset and/or a subset of the analyte and interference information contained in C. In practice, if additive correction is desired, the offset correction and a correction for only s subset of C and G will be used. The offset-corrected input spectra may be considered as $$Z = T*L' + E$$

where $L' = P' - h*l - T*C^{*}*G^{*'}$. Use of singular value decomposition (PCA) can partition the uncentered L' into two components, $$L' = U*V'$$

where U= is a matrix of eigenvalues and V' is a matrix of eigenvectors. By substitution, $$Z = T*U*V' + E$$

The product T*U produces offset and interferent corrected scores and V' is the matrix of corresponding spectra loadings associated with the corrected scores.

Multiplicative correction of the offset and interferent corrected data Z can be found in the following way:

Let S be the diagonal matrix containing the elements of the product T*d. The fully corrected spectral data are found by $$S^{-1}*Z = S^{-1}*T*U*V' + S^{-1}*E$$

where $S^{-1}$ is the inverse of S. The fully corrected score matrix W is found in a similar fashion, $$W = S^{-1}*T*U$$

$W = (W_{i1})$ is the matrix of the offset, multiplicative, and interferent corrected scores which can be used as regressors in additive mixture models etc.

It is also possible to obtain a set of scores which are corrected only for multiplicative effects by following the same method, $$W = S^{-1}*T$$

The above methods may be used for calibration, prediction, and determination procedures. Using either of the above two techniques, calibration occurs in the following way:

1. Applying a bilinear model to a set of spectral data in a calibration data set, decompose the spectral data into the factor scores T and the factor loadings P;
2. Using a statistical method (e.g. weighted least squares), a reference spectra r, and appropriate analytes and interferents G, calculate d, h, and C from P;
3. If the spectral scores are to be corrected, calculate U (for additive and interferent effects) and $S^{-1}$ (for multiplicative effects);
4. Correct the spectral input data after calculating $b_i$, $a_i$, $a_{mean}$, and $b_{mean}$, $$Y_i = [X_i - T*C^{*}*G^{*'} - a_i + a_{mean}] * b_{mean}/b_i;$$

or correct the spectral scores, $$W = S^{-1}*T*U;$$

5. Use the corrected spectral data Y fit a linear model. Methods for achieving this model include multiple linear regression, generalized least squares, maximum likelihood regression, robust regression, estimated best linear predictor, partial least squares, principal component regression, Fourier regression, and other techniques.

Alternately, use the corrected spectral scores W to fit a linear model using an appropriate method listed above.

Prediction occurs in the following way:

1. Use an independent set of data and apply the factor loadings P to find a new set of spectral scores T;
2. To use corrected spectra data, calculate a and b from the new spectral scores and use $a_{mean}$, $b_{mean}$, $C^*$ and $G^*$ derived from the calibration to determine $$Y_i = [X_i - C^{*}*G^{*'} + a_{mean} - a_i] * b_{mean}/b_i;$$

Alternatively, to use corrected spectral scores, calculate a new $S^{-1}$ from the new spectral scores and use U from the calibration data to find $$W = S^{-1}*T*U;$$

3. Use the corrected data and the calibration model coefficients from the linear model to predict the properties of interest.

Figure 5:
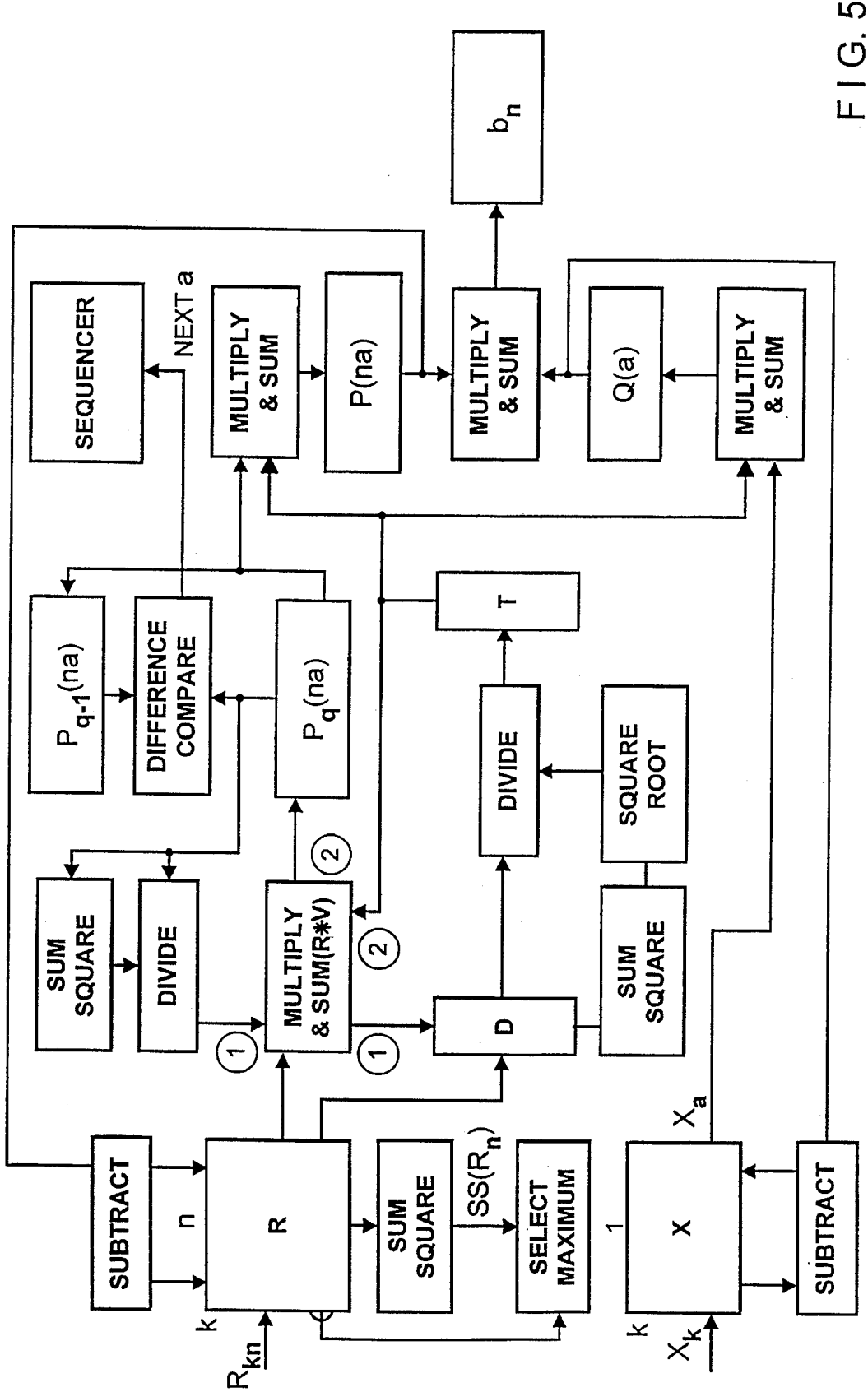
FIG. 5 is a block diagram of a principal component regression device used in conjunction with the present invention.

In the description of the alternative embodiments described immediately above (pp. 35–40), the apparatus described generally in FIG. 2 still is applicable as would be understood by one of ordinary skill. In construction of some of the more detailed blocks, the coefficient estimator 320 described above is preferably the basic element. For example, the estimation of an additive model (p. 35, step 2), is performed by coefficient estimator 320. The reconstruction of the spectral data (p. 35, step 3), is preferably performed by calculator 330. The iteration required on page 35, step 5 is controlled by a logic sequencer 370 or equivalent. Modeling from statistical analyses (principal component analysis or partial least squares, for example) may be accomplished by the structure shown in FIG. 5. Decomposition of loadings (see page 37) may be performed by the coefficient estimator 320. Other functions are readily performed by apparatus disclosed herein.

While the foregoing description and drawings represent the preferred embodiments of the present invention, it will be obvious to those skilled in the art that various changes and modifications may be made therein without departing from the true spirit and scope of the present invention.

What is claimed is:

1. A method for correcting signals representing input spectral data ($X_{ki}$) derived from a sensor during a measurement, at least as to multiplicative errors, said method comprising the steps of:

provide a first and primary reference spectrum signal ($P_{ko}$) representing a predetermined standard for such data;

providing at least one second reference spectrum signal ($P_{ka}$ or $P_{kj}$);

estimating coefficients for a selected appropriate model to be applied to said input data based on said first and second reference spectra signals; and correcting said signals representing said spectral data based on said estimated coefficients at least as to multiplicative errors for producing signals representing a linear additive structure for use in calibration, validation and determination by linear multivariate analysis.

2. The method as in claim 1 wherein said at least one second reference spectrum signal represents expected influence of analytes of interest on input data ($P_{ka}$).

3. The method as in claim 1 wherein said at least one second reference spectrum signal represents expected influence of undesired interferences (Pjk).

4. The method as in claim 1 wherein said at least one second reference spectrum signal represents expected influence of analytes of interest on the input data ($P_{ka}$) and said method also includes the step of providing at least one third reference spectrum signal ($P_{kj}$) representing the expected influence of various undesired interferences, said estimating step being also based on said at least one third reference spectrum.

5. The method as in claim 1 or claim 2 or claim 3 or claim 4 also including the step of correcting said spectral data as to additive errors based on said estimated coefficients.

6. A method of claim 5 wherein said model includes a generalized least squares technique.

7. The method as in claim 1 wherein said model is a linear model.

8. The method of claim 6 wherein said model includes a maximum likelihood regression technique.

9. The method of claim 6 wherein said model includes an estimated best linear predictor technique.

10. The method of claim 6 wherein said model includes a principal component regression technique.

11. The method of claim 6 wherein said model includes a covariance adjustment technique.

12. The method of claim 1 wherein said model is a non-linear model.

13. The method of claim 12 wherein said model includes a Taylor expansion technique.

14. The method of claim 12 wherein said model includes a steepest descent method.

15. The method of claim 12 wherein said model includes a Marquardt's compromise technique.

16. The method of claim 12 wherein said model includes a simplex optimization technique.

17. The method as in claim 1 or claim 3 or claim 4 including the steps of using the coefficients of at least one interfering component derived by the modeling to scale the spectra of the component and subtracting the scaled spectra from the data to remove their contribution from the data.

18. The method as in claim 17 including the steps of generating modified reference spectra of interfering components that contain only those portions of original reference spectra of the interfering components that are orthogonal to, and therefore uncorrelated with, at least one reference analyte spectrum, using the coefficients generated from said orthogonal reference spectrum to scale the original reference spectra prior to subtracting the scaled spectra from the data.

19. The method as in claim 18 including the step of further scaling the spectra of the interfering components to control a degree of spectral modification and correction applied to the data.

20. The method as in claim 17 including the step of further scaling the spectra of analyte data.

21. The method as in claim 1 or claim 2 or claim 3 or claim 4 or claim 7 also including the step of updating of standard ($P_{ka}$), analyte $P_{ka}$, or interference $P_{kj}$ spectra based on results of later stages of data processing and analysis.

22. The method as in claim 21 wherein said later stages of data processing and analysis include principal components analysis (PCA).

23. The method as in claim 21 wherein said later stages of data processing and analysis include a technique of partial least squares (PLS).

24. The method as in claim 1 or claim 2 or claim 3 or claim 4 or claim 17 including the step of interactively displaying graphical output concerning which analytes and interference spectra, if any, are causing difficulties with respect to estimation of the multiplicative correction and interactive control over which reference spectra are utilized, a spectral range included in estimating the coefficients and weighing of additive corrections employed.

25. The method as in claim 24 including the step of further scaling the spectra of interfering components to control a degree of spectral modification and correction applied to the data.

26. The method as in claim 24 also including the step of further scaling the spectra of analyte data.

27. The method as in claim 1 or claim 2 or claim 3 or claim 4 or claim 17 also including the step of updating of standard $P_{ka}$, analyte $P_{ka}$, and signal $P_{kj}$ spectra based on results of later stages of data processing and analysis.

28. Apparatus for correcting input spectral data ($X_{ki}$) derived from a sensor during a measurement, at least as to multiplicative errors, said apparatus comprising:

input means for supplying a signal representing spectral data subject to correction for at least multiplicative errors;

means for supplying a signal representing a first and primary reference spectrum ($P_{ko}$) as a predetermined standard for such data;

means for supplying a signal representing at least one second reference spectrum ($P_{ka}$ or $P_{kj}$);

means for estimating coefficients for a selected model for application to said input spectral data, said input spectral data signal and first and second reference spectrum signals being supplied to said estimating means; and means responsive to said estimating means for correcting said spectral data based on estimated coefficients at least as to multiplicative errors for producing a signal representing a linear additive structure for use in calibration, validation and determination by linear multivariate analysis.

29. Apparatus as in claim 28 wherein said means for supplying said signal representing at least one second reference spectrum supplies a signal which represents at least one spectrum representing expected influence of analytes of the interest on input data ($P_{ka}$).

30. Apparatus as in claim 28 wherein said means for supplying said signal representing at least one second reference spectrum supplies a signal which represents at least one spectrum representing expected influence of various undesired interferences ($P_{jk}$).

31. Apparatus as in claim 28 wherein said means for supplying said signal representing at least one second reference spectrum supplies a signal which represents at least one spectrum representing expected influence of analytes of interest of input data and also including means for supplying a signal of at least one third reference spectrum representing expected influence of various undesired interferences, said third reference spectrum signal also being supplied to said estimating means.

32. Apparatus as in claim 28 or claim 29 or claim 30 or claim 31 including means responsive to said estimating means for correcting said spectral data as to additive errors based on said estimated coefficients.

33. Apparatus as in claim 28 or claim 29 or claim 30 or claim 31 wherein said estimating means estimates coefficients for a linear model.

34. Apparatus as in claim 28 or claim 29 or claim 30 or claim 31 wherein said estimating means estimates coefficients for a non-linear model.

35. In a system for analyzing a medium, said system having a spectrophotometric sensor for providing a signal representing input spectral data ($X_{ki}$), the improvement comprising:

apparatus for correcting said spectral data for at least multiplicative errors, said apparatus including:

means for supplying a signal representing a first and primary reference spectrum ($P_{ko}$) as a predetermined standard for said spectral data;

means for supplying a signal representing at least one second reference spectrum ($P_{ka}$ or $P_{kj}$);

means for estimating coefficients for a selected model for application to said input spectral data, said input spectral signals and first and second reference spectral signals being supplied to said estimating means; and means responsive to said estimating means for correcting said spectral data based on estimated coefficients at least as to multiplicative errors for producing a signal representing a linear additive structure for use in calibration, validation and determination based on linear multivariate analysis.

36. The method for correcting input spectral data ($X_{ki}$) derived from a measurement, by applying an additive model and multiplicative model for the data in a sequential fashion, comprising the steps of:

1) obtaining a set of spectral data Z from original input spectral data corrected for multiplicative effects by using a standard multiplicative scatter correction technique;

2) estimating an additive model which takes into account spectral variations of analytes and interferences;

3) reconstructing spectral data Y without the estimated additive effects;

4) estimating the multiplicative effects on Y;

5) constructing a new matrix of corrected spectra Z from X; and repeating steps 2, 3 and 4 until convergence occurs.

37. The method of claim 36 wherein the additive effects are obtained from a different model than the multiplicative effects.

38. The method of claim 37 wherein one model is a physical model and the other model is a chemical model.

39. The method of claim 36 wherein step 4 includes the steps of:

providing a first and primary reference spectrum;

providing at least one second reference spectrum;

estimating coefficients for a selected appropriate model to be applied to the input data based on said first and second reference spectra; and correcting said spectral data Y based on said estimated coefficients.

40. The method for correcting input spectral data ($X_{ki}$) derived from a measurement or for correcting the scores obtained by bilinear modeling of such data, said method comprising the steps of:

examining the measured spectral data as a combined additive and multiplicative structure such that $$X=T*P'+E$$

where $X=(x_{ik})$ is the matrix of spectral ordinates for $i=1,2 \ldots N$ objects, $k=1,2 \ldots, K$ wavelengths, $T=(t_{il})$ is the matrix of scores for objects i, $l=1,2 \ldots L$ representing bilinear factors Obtained from a bilinear model, $P=(P_{ki})$ are the loadings for objects i on bilinear factors l, and $E=(e_{ik})$ are the residuals between data X and model $T*P'$;

decomposing the loadings into a function of a reference spectral and, optionally, a matrix of spectral components for analyte and interference phenomena;

obtaining the additive and multiplicative effects for the input spectra from the coefficients from the loading decomposition and scores; and correcting said input spectra based on said obtained additive and multiplicative effects.

41. The method of claim 40 including the step of correcting said input spectral data simultaneously for interferent contributions and additive and multiplicative effects.

42. The method for correcting input spectral data ($X_{ki}$) derived from a measurement or for correcting the scores obtained by bilinear modeling of such data, said method comprising the steps of:

examining the measured spectral data as a combined additive and multiplicative structure such that $$X=T*P'+E$$

where $X=(x_{ik})$ is the matrix of spectral ordinates for $i=1,2 \ldots N$ objects, $k=1,2 \ldots, K$ wavelengths, $T=(t_{il})$ is the matrix of scores for objects i, $l=1,2 \ldots L$ representing bilinear factors obtained from a bilinear model, $P=(P_{ki})$ are the loadings for objects i on bilinear factors l, and $E=(e_{ik})$ are the residuals between data X and model $T*P'$;

decomposing the loadings into a function of a reference spectrum and, optionally, a matrix of spectral components for analyte and interference phenomena;

obtaining the additive effects for the scores T from the offset corrected loadings and the scores T; and applying the obtained additive effects to the scores;

obtaining the multiplicative effect from the coefficient d from the reference spectrum; and obtaining scores corrected for additive and multiplicative effects using the multiplicative effect, or scores T and, optionally, the additive effect.

43. The method of claim 42 including the steps of additionally correcting the input spectral data for multiplicative effects.

44. The method of claim 36 or claim 39 or claim 41 including the further step of using said corrected input spectral data or said corrected scores for calibration of measuring equipment, prediction and determination procedures.

45. The method of claim 44 wherein the prediction procedure, using corrected spectral data, includes the steps of:
   using an independent set of data and applying factor loadings P to find a new set of spectral scores T; and
   determining the additive and multiplicative effects from the new spectral scores and using the mean quantities of additive and multiplicative effects and those portions of the interferents and analytes which had been used in a prior calibration to obtain a corrected spectra; and
   using the corrected data and the calibration model coefficients from the linear model coefficients from the linear model to predict properties of interest.

46. The method of claim 44 wherein the prediction procedure, using corrected spectral scores, includes the steps of:
   using an independent set of data and applying factor loadings P to find a new set of spectral scores T; and
   determining an $S^{-1}$ factor related to a matrix containing T*d for multiplicative effects from the new spectral scores T and using a factor U from calibration relating to additive and interferent effects to find
   $W=S^{-1}*T*U$; where W is the matrix of the additive, multiplicative and interferent corrected scores which can be used as regressors in additive mixture models;
   using the corrected data and calibration model coefficients from the linear model to predict properties of interest.

47. Apparatus for correcting an input spectral data $(X_{ki})$ signal derived from a measurement, particularly as to multiplicative errors, by the fitting of an additive model and multiplicative model in sequential fashion, comprising:
   first means for obtaining a signal representing a set of spectral data Z from the original input spectral data signal corrected for multiplicative effect by using a standard multiplicative scatter correction technique;
   second means for providing a signal representing estimate of an additive model which takes into account spectral variations of analytes and interferences;
   third means for providing a signal representing the reconstructing of spectral data Y without the estimated additive effects;
   fourth means for providing a signal representing an estimate of the multiplicative effects on Y;
   fifth means for providing a signal representing the construction of a new matrix of corrected spectra Z from X;
   means for respectively providing said signal from said fifth means to said second, third and fourth means; and
   means responsive to the output signals of said second, third and fourth means for determining when convergence occurs.

48. Apparatus for correcting an input spectral data $(X_{ki})$ signal derived from a measurement or for correcting a signal representing the scores obtained by bilinear modeling of such data, comprising:
   means for providing a signal responsive to said input signal representing the measured spectral data as a combined additive and multiplicative structure such that $$X=T*P'+E$$

where $X=(x_{ik})$ is the matrix of spectral ordinates for i=1,z . . . N objects, k=1,2 . . . , k wavelengths, $T=(t_{il})$ is the matrix of scores for objects i, l=1,2 . . . L representing bilinear factors obtained from a bilinear model, $P=(P_{kl})$ are the loadings for objects i on bilinear factors l and $E=(e_{ik})$ are the residuals between data X and model T*P';
   means for providing a signal representing decomposed loadings which have been decomposed into a function of a reference spectra and, optionally, a matrix of spectral components for analyte and interference phenomena;
   means for providing a signal representing the additive and multiplicative effects for the input spectra obtained from the coefficients from the loading decomposition and scores; and
   means for providing a signal representing the correction of said input spectra from said signal representing the additive and multiplicative effects.

49. Apparatus for correcting an input spectral data $(X_{ki})$ signal derived from a measurement or for correcting a signal representing the scores obtained by linear modeling of such data, comprising:
   means for providing a signal responsive to said input signal representing the measured spectral data as a combined additive and multiplicative structure such that $$X=T*P'+E$$

where $X=(x_{ik})$ is the matrix of spectral ordinates for i=1,z . . . N objects, k=1,2 . . . , k wavelengths, $T=(t_{il})$ is the matrix of scores for objects i, l=1,2 . . . L representing bilinear factors obtained from a bilinear model, $P=(P_{kl})$ are the loadings for objects i on bilinear factors l and $E=(e_{ik})$ are the residuals between data X and model T*P';
   means for providing a signal representing decomposed loadings which have been decomposed into a function of a reference spectra and, optionally, a matrix of spectral components for analyte and interference phenomena;
   means for providing a signal representing the additive effects for the scores T obtained from the offset corrected loadings and the scores T;
   means responsive to said signal representing the additive effects for providing a signal representing the application of the additive effects to the multivariate scores;
   means for providing a signal representing the multiplicative effect from the coefficient d from the reference spectrum; and
   means for providing a signal representing scores corrected for additive and multiplicative effects using the multiplicative effect, or scores T and, optionally the additive effect.

\* \* \* \* \*